US012766099B2

(12) United States Patent
Wang et al.

(10) Patent No.: US 12,766,099 B2
(45) Date of Patent: Oct. 20, 2026

(54) PHARMACEUTICAL COMPOSITION, PREPARATION METHOD THEREFOR AND APPLICATION THEREOF

(71) Applicants: Guangzhou Ocusun Ophthalmic Biotechnology Co., Ltd., Guangzhou (CN); Ocusun Ophthalmic Pharmaceutical (Guangzhou) Co., Ltd., Guangzhou (CN)

(72) Inventors: Yandong Wang, Guangzhou (CN); Yingxue Su, Guangzhou (CN); Chen Cao, Guangzhou (CN); Sheng'an Zhou, Guangzhou (CN); Yaping Xue, Guangzhou (CN); Meirong Wu, Guangzhou (CN); Chuiliang Yu, Guangzhou (CN)

(73) Assignees: Guangzhou Ocusun Ophthalmic Biotechnology Co., Ltd., Guangzhou (CN); Ocusun Ophthalmic Pharmaceutical (Guangzhou) Co., Ltd., Guangzhou (CN)

( * ) Notice: Subject to any disclaimer, the term of this patent is extended or adjusted under 35 U.S.C. 154(b) by 322 days.

(21) Appl. No.: 18/682,112

(22) PCT Filed: Aug. 17, 2022

(86) PCT No.: PCT/CN2022/113025
§ 371 (c)(1),
(2) Date: Feb. 7, 2024

(87) PCT Pub. No.: WO2023/020536
PCT Pub. Date: Feb. 23, 2023

(65) Prior Publication Data

US 2025/0120910 A1 Apr. 17, 2025

(30) Foreign Application Priority Data

Aug. 18, 2021 (CN) ......................... 202110951364.8

(51) Int. Cl.

| | |
|---|---|
| ***A61K 9/107*** | (2006.01) |
| ***A61K 9/00*** | (2006.01) |
| ***A61K 9/08*** | (2006.01) |
| ***A61K 31/575*** | (2006.01) |
| ***A61K 47/02*** | (2006.01) |
| ***A61K 47/10*** | (2017.01) |
| ***A61K 47/18*** | (2017.01) |
| ***A61K 47/26*** | (2006.01) |
| ***A61K 47/38*** | (2006.01) |
| ***A61K 47/44*** | (2017.01) |
| ***A61P 27/02*** | (2006.01) |

(52) U.S. Cl.
CPC ............ *A61K 9/107* (2013.01); *A61K 9/0048* (2013.01); *A61K 9/08* (2013.01); *A61K 31/575* (2013.01); *A61K 47/02* (2013.01); *A61K 47/10* (2013.01); *A61K 47/186* (2013.01); *A61K 47/26* (2013.01); *A61K 47/38* (2013.01); *A61K 47/44* (2013.01); *A61P 27/02* (2018.01)

(58) Field of Classification Search
CPC ........ A61K 9/107; A61K 9/0048; A61K 9/08; A61K 47/02; A61K 47/10; A61K 47/186; A61K 47/26; A61K 47/38; A61K 47/44; A61K 31/575; A61P 27/02
See application file for complete search history.

(56) References Cited

U.S. PATENT DOCUMENTS

2020/0360403 A1 11/2020 Sciamanna

FOREIGN PATENT DOCUMENTS

| | | | | | |
|---|---|---|---|---|---|
| CN | 106344587 | A | * | 1/2017 | ............... A61K 9/08 |
| CN | 108472303 | A | | 8/2018 | |
| CN | 109364020 | A | | 2/2019 | |
| CN | 113413415 | A | | 9/2021 | |
| CN | 114129574 | A | | 3/2022 | |
| CN | 114129575 | A | | 3/2022 | |
| EP | 3828193 | A1 | * | 6/2021 | ................ C07J 9/00 |
| EP | 3536698 | B1 | | 8/2021 | |
| JP | 2010265261 | A | | 11/2010 | |
| JP | 2016147889 | A | | 8/2016 | |
| JP | 2020-503379 | A | | 1/2020 | |

(Continued)

OTHER PUBLICATIONS

Nagai et al., "The Intravitreal Injection of Lanosterol Nanoparticles Rescues Lens Structure Collapse at an Early Stage in Shumiya Cataract Rats" in International Journal of Molecular Sciences, vol. 21, Issue 3, Feb. 2020. (Year: 2020).*
Tamura, "The 18th revised edition of the Japanese Pharmacopoeia", Mar. 7, 2021, all enclosed pages cited.
Jiang, Jing et al., The Great Western Exploration of Floaters [J]. Science and Technology Wind, 2020,(6):197. DOI 10.19392/j.cnki. 1671-7341.202006179.

*Primary Examiner* — Blessing M Fubara
(74) *Attorney, Agent, or Firm* — FULLER IP LAW LLC; Rodney J. Fuller

(57) ABSTRACT

A pharmaceutical composition, a preparation method therefor and an application thereof. The pharmaceutical composition comprises the following components: a compound represented by formula I, hydroxypropyl methyl cellulose, benzalkonium chloride, and a pH regulator. The pharmaceutical composition can be used for preparing drugs for preventing or treating cataracts. The pharmaceutical composition has excellent stability in respect of exposure to light and to high temperatures, can be stored at room temperature, is convenient for patients to use, has pH and osmotic pressure close to those in the intraocular environment, is uniform in particle size distribution, and thus can give the patients good comfort.

17 Claims, No Drawings

(56) References Cited

FOREIGN PATENT DOCUMENTS

| | | | |
|---|---|---|---|
| WO | 2007108541 | A1 | 9/2007 |
| WO | 2018/036522 | A1 | 3/2018 |
| WO | 2020/020306 | A1 | 7/2019 |
| WO | 2020/177714 | A1 | 9/2020 |

* cited by examiner

PHARMACEUTICAL COMPOSITION, PREPARATION METHOD THEREFOR AND APPLICATION THEREOF

CROSS-REFERENCE TO RELATED APPLICATIONS

The present application is the U.S. National Stage of International Patent Application No. PCT/CN2022/113025, filed Aug. 17, 2022, which claims the benefit of and priority to Chinese Patent Application No. 202110951364.8, filed Aug. 18, 2021, the contents of each of which are incorporated herein by reference in their entireties.

TECHNICAL FIELD

The present invention belongs to the field of medicine, specifically relates to a pharmaceutical composition, a preparation method therefor and an application thereof.

BACKGROUND

Cataracts is a disease of the eye that occurs on the lens inside the eyeball, and the opacity of the lens is collectively called cataracts. All of aging, genetics, metabolic abnormalities, trauma, radiation, poisoning, and local malnutrition can cause damage to the lens capsule, increase its permeability, lose its barrier effect, or lead to lens metabolism disorders, denature the lens protein to form opacity. If the lens of the eyeball changes from transparent to opaque, affecting the illumination received by the eye, it will affect the eye's vision. The impact on vision is less severe when the opacity is mild, and as the degree of opacity progresses, the vision decreases, leading to blindness in severe cases. Cataracts is one of the most common causes of blinding eye and is a major cause of blindness. Because the mechanism of cataracts formation is still unclear, no breakthrough has been made in drug treatment so far. Therefore, the only known effective treatment is surgery currently.

Although the continuous advancement of cataracts surgery has provided great help for the treatment of cataracts, the cure rate of surgical treatment is still far lower than the incidence rate, and there is a possibility of serious complications. On the other hand, cataracts surgery is very expensive and places a huge burden on patients and the health insurance system. Therefore, the prevention and treatment with drugs plays an important role.

At present, the clinical drugs for the treatment of cataracts include: (1) aldose reductase inhibitors, such as Cataline (Catalin, Pirenoxine Eye Drops, Pirenoxine Sodium Eye Drops), Phacolysin, Bendazac L-lysine, etc.; (2) antioxidant damage drugs, such as glutathione, taurine, aspirin, etc.; (3) nutritional metabolism drugs, such as vitamins, carotenoids, etc.; (4) traditional Chinese medicine composition, including ShiHu YeGuangWan, QijuDihuangWan, ShiJueMing-San, etc. However, these drugs for the treatment of cataracts have been proven by long-term clinical trials that can only delay the deterioration of cataracts, but cannot reverse the condition to treat cataracts. Therefore, there is a great clinical need for new varieties of ophthalmic topical anti-cataracts drugs that are safe, and have good efficacy, strong intraocular penetration, and stable properties.

Lanosterol is an amphiphilic molecule enriched in the lens, which is synthesized by a key cyclization reaction of lanosterol synthase (LSS) in the cholesterol synthesis pathway, which can reduce the abnormal aggregation of lens proteins, make them rearrange and restore crystal transparency. It has been shown that lanosterol synthase can be detected in the lens. In addition, in the Shumiya cataracts rat study, a homozygous mutation-specific combination of lanosterol synthase and farnesyl diphosphate farnesyltransferase 1 (FDFT1) attenuated the level of cholesterol in the lens and caused cataracts. In addition, lanosterol can significantly reduce the preformed lens protein aggregates in vitro and at the cellular levels; it has also been confirmed in vivo that lanosterol can reverse the condition of cataracts, making the lens clear and transparent, and is a new molecule for the prevention and treatment of cataracts.

It is disclosed in WO2020177714 a formulation of a lanosterol prodrug compound that can reduce cataracts symptoms, improve lens clarity, and lens GSH-PX activity. However, the preparation process of the formulation is complex to operate, the stability is poor, it is not easy to store at room temperature, and patients find that the comfort level is not good when using it. Therefore, there is an urgent clinical need to develop a composition or formulation with a simple preparation process, strong stability, and better comfort level for patients.

SUMMARY

In view of the deficiencies of the prior art, an object of the present invention is to provide a pharmaceutical composition, a preparation method therefor and a use thereof. The pharmaceutical composition has excellent stability in respect of exposure to light and high temperature and can be used to prepare a medicament for preventing or treating cataracts or floaters.

To achieve this purpose, the present invention adopts the following technical solutions.

In the first aspect, the present invention provides a pharmaceutical composition comprising the following components:

a compound of formula I, hydroxypropyl methylcellulose, benzalkonium chloride and a pH regulator;

formula I

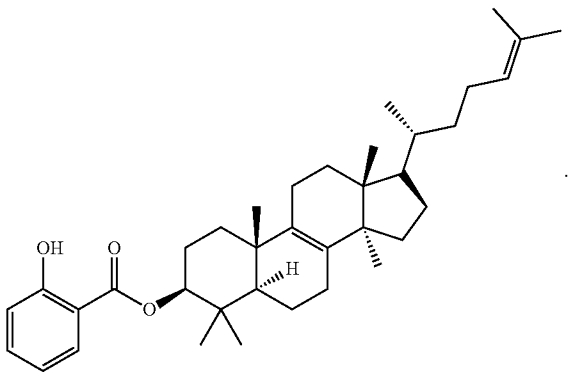

It is found and developed according to the present invention that the stability of the compound of formula I can be significantly improved by combining the compound of formula I with hydroxypropyl methylcellulose (HPMC), benzalkonium chloride and a pH regulator, so as to obtain a pharmaceutical composition with stable quality.

In some embodiments of the present invention, the pharmaceutical composition comprises the components with the following parts by weight:

0.01~4 parts of compound of formula I (for example, it can be 0.01 parts, 0.05 parts, 0.1 parts, 0.3 parts, 0.5 parts, 0.8 parts, 1 part, 1.5 parts, 2 parts, 2.5 parts, 3 parts, 3.5 parts or 4 parts, etc.), 2~12 parts of hydroxypropyl methylcellulose (for example, it can be 2 parts, 3 parts, 5 parts, 8 parts, 10 parts or 12 parts, etc.), 0.05~0.06 parts of benzalkonium chloride (for example, it can be 0.05 parts, 0.052 parts, 0.053 parts, 0.055 parts, 0.056 parts, 0.058 parts or 0.06 parts, etc.) and 1~20 parts of pH regulator (for example, it can be 1 part, 2 parts, 3 parts, 5 parts, 8 parts, 10 parts, 12 parts, 15 parts, 18 parts or 20 parts, etc.); and the pH of the pharmaceutical composition is 6 to 8, for example it can be 6, 6.2, 6.5, 6.8, 7, 7.2, 7.5, 7.8 or 8, etc.

In some embodiments of the present invention, the concentration of the compound of formula I in the pharmaceutical composition is 0.01~4 mg/mL, and preferably 0.1 mg/mL, 0.2 mg/mL, 0.3 mg/mL, 0.4 mg/mL, 0.5 mg/mL, 1 mg/mL, 2 mg/mL, 3 mg/mL or 4 mg/mL.

In some embodiments of the present invention, the pH regulator is selected from one or a combination of at least two of the group consisting of sodium hydroxide, hydrochloric acid, sodium citrate, citric acid, boric acid, borax, sodium dihydrogen phosphate, disodium hydrogen phosphate, potassium dihydrogen phosphate and dipotassium hydrogen phosphate.

In some embodiments of the present invention, the pharmaceutical composition further comprises a solubilizer.

In some embodiments of the present invention, the parts by weight of the solubilizer in the pharmaceutical composition is 10~50 parts; for example, it can be 10 parts, 15 parts, 20 parts, 25 parts, 30 parts, 35 parts, 40 parts, 45 parts or 50 parts, etc.

In some embodiments of the present invention, the solubilizer is selected from one or a combination of at least two of the group consisting of polysorbate-80, glycerol, hydrogenated castor oil-RH40, polyethylene glycol 400, hydroxypropyl-ß-cyclodextrin and poloxamer 188.

In some embodiments of the present invention, the pharmaceutical composition comprises the components with the following parts by weight:

2 parts of compound of formula I, 6 parts of hydroxypropyl methylcellulose, 16.5 parts of boric acid, 2 parts of borax and 0.05 parts of benzalkonium chloride; or 2 parts of compound of formula I, 6 parts of hydroxypropyl methylcellulose, 40 parts of polysorbate-80, 16 parts of boric acid, 1.6 parts of borax and 0.05 parts of benzalkonium chloride; or 2 parts of compound of formula I, 6 parts of hydroxypropyl methylcellulose, 10 parts of hydrogenated castor oil-RH40, 17 parts of boric acid, 1.7 parts of borax and 0.05 parts of benzalkonium chloride.

In the second aspect, the present invention provides a pharmaceutical composition comprising the components with the following parts by weight:

2 parts of compound of formula I, 6 parts of hydroxypropyl methylcellulose, 25 parts of glycerol and 0.05 parts of benzalkonium chloride; or 2 parts of compound of formula I, 6 parts of hydroxypropyl methylcellulose, 10 parts of hydrogenated castor oil-RH40, 40 parts of polysorbate-80, 25 parts of glycerol, and 0.05 parts of benzalkonium chloride.

In some embodiments of the present invention, the particle size of the compound of formula I is <90 μm, and preferably is ≤50 μm.

In some embodiments of the present invention, the particle size distribution of the compound of formula I is $D_{90}$≤7 μm and/or $D_{50}$≤4 μm.

In some embodiments of the present invention, the particle size of $D_{90}$ of the compound of formula I is <8 μm.

In some embodiments of the present invention, the particle size of $D_{50}$ of the compound of formula I is ≤3.5 μm.

In some embodiments of the present invention, the dosage form of the pharmaceutical composition is a suspension, an emulsion or a gel, and preferably an emulsion.

In the third aspect, the present invention provides a preparation method for the pharmaceutical composition as described in the first or second aspect, and the preparation method comprises: mixing evenly the compound of formula I, hydroxypropyl methylcellulose, benzalkonium chloride, the optional pH regulator and the optional solubilizer according to the prescription amount to obtain the pharmaceutical composition.

It should be noted that the term "optional" as used in the present invention refers to the presence or absence of a corresponding component. When the pharmaceutical composition contains a corresponding component, the component is used in the preparation method, and when the pharmaceutical composition does not contain the corresponding component, the component is not used in the preparation method.

In some embodiments of the present invention, the preparation method comprises the following steps:

(1) dissolving hydroxypropyl methylcellulose with water for injection to obtain solution I;

(2) dissolving the components other than hydroxypropyl methylcellulose and the compound of formula I in prescription amount with water for injection, then adding to the solution I, and mixing evenly to obtain solution II;

(3) taking a prescription amount of the compound of formula I, adding to the solution II, and mixing evenly to obtain solution III; and (4) filling the solution III to full volume with water for injection to obtain the pharmaceutical composition.

Preferably, the preparation method comprises the following steps:

(1) dissolving hydroxypropyl methylcellulose with water for injection, and stirring to dissolve completely to obtain solution I;

(2) dissolving the components other than hydroxypropyl methylcellulose and the compound of formula I in prescription amount with water for injection, then adding to the solution I, adding water for injection to 90% of the prescription amount, and stirring well to obtain solution II;

(3) taking a prescription amount of the compound of formula I, and adding to the solution II to obtain solution III;

(4) homogenizing the solution III with a high-pressure homogenizer to obtain solution IV; and (5) filling the solution IV to full volume with water for injection to obtain the pharmaceutical composition.

In the fourth aspect, the present invention provides a use of the pharmaceutical composition as described in the first or second aspect in the preparation of a medicament for the prevention or treatment of cataracts or floaters.

Compared with the prior art, the present invention has the following beneficial effects:

The pharmaceutical composition provided according to the present invention can be used to prevent or treat cataracts and floaters. After the pharmaceutical composition was placed under a condition of 4500Lx illumination or a high-temperature condition of 60° C. for 10 days, the pH and osmotic pressure of the pharmaceutical composition remained stable, the relevant substances and contents had no obvious change. The pharmaceutical composition has excellent stability in respect of exposure to light and high temperature, can be stored at room temperature, and is convenient for patients to use. At the same time, the pharmaceutical composition has a pH and osmotic pressure close to those in the intraocular environment, is uniform in particle size distribution, has $D_{50}$ particle size not exceeding 3.5 μm, and thus can give the patient good comfort.

DETAILED DESCRIPTION

The technical solution of the present invention is further described below by specific embodiments. Those skilled in the art should be aware that the specific embodiments are merely to aid in understanding the present invention and should not be regarded as a specific limitation of the present invention.

Example 1

The present example provides a pharmaceutical composition with the components shown in the following table:

| Components | Amount (g) |
|---|---|
| Compound of formula I | 2.0 |
| HPMC | 6.0 |
| Boric acid | 16.5 |
| Borax | 2 |
| Benzalkonium chloride | 0.05 |
| Water | volume up to 1000 mL |

The preparation method for the pharmaceutical composition in this example is as follows:

(1) hydroxypropyl methylcellulose was dissolved with 10% boiling water for injection, added with an appropriate amount of cold water for injection, and stirred to dissolve completely to obtain solution I;

(2) boric acid, borax and benzalkonium chloride in prescription amount were dissolved under stirring with an appropriate amount of water for injection, then added to solution I, added with water for injection to 90% of the prescription amount, and stirred evenly to obtain solution II;

(3) the prescription amount of the compound of formula I was weighed, added to solution II, dispersed at a speed of 10000 r/min with a high-shear emulsifier for 10 minutes, and dispersed evenly to obtain solution III;

(4) the solution III was homogenized with a high-pressure homogenizer at a pressure of 250 bar once, the liquid medicine was collected, the pipeline of the high-pressure homogenizer was rinsed with an appropriate amount of sterile water for injection, the rinsing solution was collected, and combined with the liquid medicine to obtain solution IV; and (5) the solution IV was filled to full volume with the sterile water for injection.

The above-mentioned pharmaceutical composition can be further prepared as an eye drop product by the following steps: the sample was taken to detect the pH, osmotic pressure and content, and after passing the quality inspection, sub-packed in low-density polyethylene pharmaceutical eye drop bottles in sterile environment with 5 mL liquid medicine per bottle.

Example 2

The present example provides a pharmaceutical composition with the components shown in the following table:

| Components | Amount (g) |
|---|---|
| Compound of formula I | 2.0 |
| HPMC | 6.0 |
| Polysorbate-80 | 40 |
| Boric acid | 16 |
| Borax | 1.6 |
| Benzalkonium chloride | 0.05 |
| Water | volume up to 1000 mL |

The preparation method for the pharmaceutical composition in this example is as follows:

(1) hydroxypropyl methylcellulose was dissolved with 10% boiling water for injection, added with an appropriate amount of cold water for injection, and stirred to dissolve completely to obtain solution I;

(2) boric acid, borax and benzalkonium chloride in prescription amount were dissolved under stirring with an appropriate amount of water for injection, then added to solution I, slowly added with the prescription amount of polysorbate-80 while stirring, added with water for injection to 90% of the prescription amount, and stirred evenly to obtain solution II;

(3) the prescription amount of the compound of formula I was weighed, added to solution II, dispersed at a speed of 10000 r/min with a high-shear emulsifier for 10 minutes, and dispersed evenly to obtain solution III;

(4) the solution III was homogenized with a high-pressure homogenizer at a pressure of 250 bar once, the liquid medicine was collected, the pipeline of the high-pressure homogenizer was rinsed with an appropriate amount of sterile water for injection, the rinsing solution was collected, and combined with the liquid medicine to obtain solution IV; and (5) the solution IV was filled to full volume with the sterile water for injection.

The above-mentioned pharmaceutical composition can be further prepared as an eye drop product by the following steps: the sample was taken to detect the pH, osmotic pressure and content, and after passing the quality inspection, sub-packed in low-density polyethylene pharmaceutical eye drop bottles in sterile environment with 5 mL liquid medicine per bottle.

Example 3

The present example provides a pharmaceutical composition with the components shown in the following table:

| Components | Amount (g) |
|---|---|
| Compound of formula I | 2.0 |
| HPMC | 6.0 |
| Hydrogenated castor oil-RH40 | 10 |
| Boric acid | 17 |
| Borax | 1.7 |

-continued

| Components | Amount (g) |
| --- | --- |
| Benzalkonium chloride | 0.05 |
| Water | volume up to 1000 mL |

The preparation method for the pharmaceutical composition in this example is as follows:

(1) hydroxypropyl methylcellulose was dissolved with 10% boiling water for injection, added with an appropriate amount of cold water for injection, and stirred to dissolve completely to obtain solution I;

(2) boric acid, borax and benzalkonium chloride in prescription amount were dissolved under stirring with an appropriate amount of water for injection, then added to solution I, slowly added with the prescription amount of hydrogenated castor oil-RH40 while stirring, added with water for injection to 90% of the prescription amount, and stirred evenly to obtain solution II;

(3) the prescription amount of the compound of formula I was weighed, added to solution II, dispersed at a speed of 10000 r/min with a high-shear emulsifier for 10 minutes, and dispersed evenly to obtain solution III;

(4) the solution III was homogenized with a high-pressure homogenizer at a pressure of 250 bar once, the liquid medicine was collected, the pipeline of the high-pressure homogenizer was rinsed with an appropriate amount of sterile water for injection, the rinsing solution was collected, and combined with the liquid medicine to obtain solution IV; and (5) the solution IV was filled to full volume with the sterile water for injection.

The above-mentioned pharmaceutical composition can be further prepared as an eye drop product by the following steps: the sample was taken to detect the pH, osmotic pressure and content, and after passing the quality inspection, sub-packed in low-density polyethylene pharmaceutical eye drop bottles in sterile environment with 5 mL liquid medicine per bottle.

Example 4

The present example provides a pharmaceutical composition with the components shown in the following table:

| Components | Amount (g) |
| --- | --- |
| Compound of formula I | 2.0 |
| HPMC | 6.0 |
| Glycerol | 25 |
| Benzalkonium chloride | 0.05 |
| Water | volume up to 1000 mL |

The preparation method for the pharmaceutical composition in this example is as follows:

(1) hydroxypropyl methylcellulose was dissolved with 10% boiling water for injection, added with an appropriate amount of cold water for injection, and stirred to dissolve completely to obtain solution I;

(2) the prescription amount of benzalkonium chloride was dissolved under stirring with an appropriate amount of water for injection, then added to solution I, slowly added with the prescription amount of glycerol while stirring, added with water for injection to 90% of the prescription amount, and stirred evenly to obtain solution II;

(3) the prescription amount of the compound of formula I was weighed, added to solution II, dispersed at a speed of 10000 r/min with a high-shear emulsifier for 10 minutes, and dispersed evenly to obtain solution III;

(4) the solution III was homogenized with a high-pressure homogenizer at a pressure of 250 bar once, the liquid medicine was collected, the pipeline of the high-pressure homogenizer was rinsed with an appropriate amount of sterile water for injection, the rinsing solution was collected, and combined with the liquid medicine to obtain solution IV; and (5) the solution IV was filled to full volume with the sterile water for injection.

The above-mentioned pharmaceutical composition can be further prepared as an eye drop product by the following steps: the sample was taken to detect the pH, osmotic pressure and content, and after passing the quality inspection, sub-packed in low-density polyethylene pharmaceutical eye drop bottles in sterile environment with 5 mL liquid medicine per bottle.

Example 5

The present example provides a pharmaceutical composition with the components shown in the following table:

| Components | Amount (g) |
| --- | --- |
| Compound of formula I | 2.0 |
| HPMC | 6.0 |
| Hydrogenated castor oil-RH40 | 10 |
| Polysorbate-80 | 40 |
| Glycerol | 25 |
| Benzalkonium chloride | 0.05 |
| Water | volume up to 1000 mL |

The preparation method for the pharmaceutical composition in this example is as follows:

(1) hydroxypropyl methylcellulose was dissolved with 10% boiling water for injection, added with an appropriate amount of cold water for injection, and stirred to dissolve completely to obtain solution I;

(2) the prescription amount of benzalkonium chloride was dissolved under stirring with an appropriate amount of water for injection, then added to solution I, slowly added with hydrogenated castor oil-RH40, polysorbate-80 and glycerol in prescription amount while stirring, added with water for injection to 90% of the prescription amount, and stirred evenly to obtain solution II;

(3) the prescription amount of the compound of formula I was weighed, added to solution II, dispersed at a speed of 10000 r/min with a high-shear emulsifier for 10 minutes, and dispersed evenly to obtain solution III;

(4) the solution III was homogenized with a high-pressure homogenizer at a pressure of 250 bar once, the liquid medicine was collected, the pipeline of the high-pressure homogenizer was rinsed with an appropriate amount of sterile water for injection, the rinsing solution was collected, and combined with the liquid medicine to obtain solution IV; and (5) the solution IV was filled to full volume with the sterile water for injection.

The above-mentioned pharmaceutical composition can be further prepared as an eye drop product by the following steps: the sample was taken to detect the pH, osmotic pressure and content, and after passing the quality inspection, sub-packed in low-density polyethylene pharmaceutical eye drop bottles in sterile environment with 5 mL liquid medicine per bottle.

Comparative Example 1

Provided is a pharmaceutical composition with the components shown in the following table:

| Components | Amount (g) |
|---|---|
| Compound of formula I | 2.0 |
| HPMC | 6.0 |
| Poloxamer 188 | 16 |
| Poloxamer 407 | 205 |
| Benzalkonium chloride | 0.05 |
| Water | volume up to 1000 mL |

The preparation method for the pharmaceutical composition is the same as that in Example 4 except that poloxamer 188 and poloxamer 407 are used instead of glycerol.

Stability Test (1) Photostability test: In order to investigate the photostability of the compositions provided by the above examples and comparative example, all samples for illumination factor investigation were packaged according to commercial standard, placed in the illumination incubator MGC-100 under a condition of 4500Lx, sampled on Day 0, Day 5, and Day 10 respectively, and tested according to the key investigation items for stability. The investigation items for stability include: traits, particle size, particle size distribution, pH value, osmotic pressure, determination of the content of compound of formula I, and determination of the content of impurities. The test results are shown in Table 1 below.

(2) High-temperature stability test: In order to investigate the high-temperature stability of the compositions provided by the above examples and comparative example, all samples for high-temperature factor investigation were packaged according to commercial standard, placed in the 101-1A digital display electric drying incubator under a condition of 60° C., sampled on Day 0, Day 5, and Day 10 respectively, and tested according to the key investigation items for stability. The investigation items for stability include: traits, particle size, particle size distribution, pH value, osmotic pressure, determination of the content of compound of formula I, and determination of the content of impurities. The test results are shown in Table 1 below.

TABLE 1

| | Investigation | | Illumination test 4500 Lx | | | High-temperature test 60° C. | | |
|---|---|---|---|---|---|---|---|---|
| Prescription | items | Limit requirements | Day 0 | Day 5 | Day 10 | Day 0 | Day 5 | Day 10 |
| Example 1 | Traits | It should be an off-white suspension liquid. | Comply with the requirement | Comply with the requirement | Comply with the requirement | Comply with the requirement | Comply with the requirement | Comply with the requirement |
| | pH value | It should be 6.0 to 8.0. | 7.04 | 7.07 | 7.03 | 7.04 | 7.05 | 7.00 |
| | Particle size | No more than two particles larger than 50 μm, and no detectable particles larger than 90 μm. | Comply with the requirement | Comply with the requirement | Comply with the requirement | Comply with the requirement | Comply with the requirement | Comply with the requirement |
| | Osmotic pressure | Osmotic pressure molar concentration should be 270 to 330 mOsmol/kg. | 282 | 282 | 281 | 282 | 280 | 282 |
| | Total Impurities (%) | Total impurities should not exceed 8.0%. | 5.49 | 5.53 | 5.81 | 5.49 | 5.10 | 5.21 |
| | Content (%) | It should be 90.0 to 110.0% of the labelled amount. | 105.86 | 103.6 | 99.12 | 105.86 | 104.56 | 99.64 |
| | Particle size distribution | $D_{10}$ (μm) | 1.161 | 1.147 | 1.175 | 1.161 | 1.154 | 1.156 |
| | | $D_{50}$ (μm) | 3.150 | 3.065 | 3.081 | 3.150 | 3.080 | 3.094 |
| | | $D_{90}$ (μm) | 6.108 | 5.919 | 5.908 | 6.108 | 5.925 | 5.957 |
| Example 3 | Traits | It should be an off-white suspension liquid. | Comply with the requirement | Comply with the requirement | Comply with the requirement | Comply with the requirement | Comply with the requirement | Comply with the requirement |
| | pH value | It should be 6.0 to 8.0. | 6.96 | 6.95 | 6.91 | 6.96 | 6.95 | 6.69 |
| | Particle size | No more than two particles larger than 50 μm, and no detectable particles larger than 90 μm. | Comply with the requirement | Comply with the requirement | Comply with the requirement | Comply with the requirement | Comply with the requirement | Comply with the requirement |
| | Osmotic pressure | Osmotic pressure molar concentration should be 270 to 330 mosmol/kg. | 292 | 293 | 291 | 292 | 293 | 305 |

TABLE 1-continued

| Prescription | Investigation items | Limit requirements | Illumination test 4500 Lx Day 0 | Day 5 | Day 10 | High-temperature test 60° C. Day 0 | Day 5 | Day 10 |
|---|---|---|---|---|---|---|---|---|
| | Total Impurities (%) | Total impurities should not exceed 8.0%. | 5.17 | 5.32 | 5.87 | 5.17 | 5.41 | 6.04 |
| | Content (%) | It should be 90.0 to 110.0% of the labelled amount. | 105.94 | 104.65 | 102.84 | 105.94 | 105.50 | 101.58 |
| | Particle size distribution | $D_{10}$ (μm) | 1.116 | 1.099 | 1.103 | 1.116 | 1.085 | 1.079 |
| | | $D_{50}$ (μm) | 2.784 | 2.779 | 2.783 | 2.784 | 2.760 | 2.775 |
| | | $D_{90}$ (μm) | 5.433 | 5.449 | 5.443 | 5.433 | 5.434 | 5.450 |
| Example 4 | Traits | It should be an off-white suspension liquid. | Comply with the requirement | Comply with the requirement | Comply with the requirement | Comply with the requirement | Comply with the requirement | Comply with the requirement |
| | pH value | It should be 6.0 to 8.0. | 6.86 | 6.99 | 6.74 | 6.86 | 6.61 | 6.28 |
| | Particle size | No more than two particles larger than 50 μm, and no detectable particles larger than 90 μm. | Comply with the requirement | Comply with the requirement | Comply with the requirement | Comply with the requirement | Comply with the requirement | Comply with the requirement |
| | Osmotic pressure | Osmotic pressure molar concentration should be 270 to 330 mosmol/kg. | 290 | 290 | 288 | 290 | 287 | 290 |
| | Total Impurities (%) | Total impurities should not exceed 8.0%. | 5.79 | 6.20 | 6.41 | 5.79 | 5.39 | 5.44 |
| | Content (%) | It should be 90.0 to 110.0% of the labelled amount. | 106.83 | 103.04 | 101.82 | 106.83 | 105.93 | 101.81 |
| | Particle size distribution | $D_{10}$ (μm) | 1.107 | 1.106 | 1.122 | 1.107 | 1.104 | 1.105 |
| | | $D_{50}$ (μm) | 2.941 | 2.855 | 2.893 | 2.941 | 2.873 | 2.861 |
| | | $D_{90}$ (μm) | 5.740 | 5.478 | 5.535 | 5.740 | 5.545 | 5.511 |
| Comparative Example 1 | Traits | It should be an off-white viscous liquid. | Comply with the requirement | Comply with the requirement | Comply with the requirement | Comply with the requirement | Comply with the requirement | Comply with the requirement |
| | pH value | It should be 6.0 to 8.0. | 7.07 | 6.90 | 6.63 | 7.07 | 3.23 | 2.91 |
| | Particle size | No more than two particles larger than 50 μm, and no detectable particles larger than 90 μm. | Comply with the requirement | Comply with the requirement | Comply with the requirement | Comply with the requirement | Comply with the requirement | Comply with the requirement |
| | Total Impurities (%) | Total impurities should not exceed 8.0%. | 5.40 | 6.28 | 6.24 | 5.40 | 5.89 | 6.67 |
| | Content (%) | It should be 90.0 to 110.0% of the labelled amount. | 101.74 | 102.17 | 101.76 | 101.74 | 101.98 | 100.68 |
| | Particle size distribution | $D_{10}$ (μm) | 1.172 | 1.181 | 1.170 | 1.174 | 1.168 | 1.171 |
| | | $D_{50}$ (μm) | 4.113 | 4.206 | 4.196 | 4.115 | 4.109 | 4.205 |
| | | $D_{90}$ (μm) | 8.077 | 8.117 | 8.098 | 8.126 | 8.119 | 8.129 |

It can be seen from the experimental results in Table 1 that after the pharmaceutical composition provided according to the present invention was placed under a condition of 4500Lx illumination or a condition of 60° C. high temperature for 10 days, the pH and osmotic pressure thereof remained stable, the relevant substances and contents had no obvious change. The pharmaceutical composition according to the present invention has more excellent stability in respect of exposure to light and high temperature than that provided in the comparative example, can be stored at room temperature, and is convenient for patients to use. At the same time, the pharmaceutical composition has a pH and osmotic pressure close to those in the intraocular environment, is uniform in particle size distribution, has a $D_{50}$ particle size not exceeding 3.5 μm, and thus can give the patients better comfort level.

In contrast, the pH value of the pharmaceutical composition obtained in comparative example 1 changed significantly under a condition of 4500Lx illumination or high temperature of 60° C., and the stability was poor. Moreover, the pharmaceutical composition obtained in comparative example 1 was a gel, and the osmotic pressure thereof cannot be measured and did not meet the requirements of the intraocular environment, and the particle sizes of $D_{50}$ and $D_{90}$ were larger, and the comfort level was poor.

Therapeutic Effect Test

Nine patients with floaters were selected and administrated with the pharmaceutical composition provided in Example 1 four times a day with 2 drops each time from the date of diagnosis, and the therapeutic effect on floaters of the patients observed on Day 15 and Day 30 are shown in Table 2 below:

TABLE 2

| Patient No. | Symptoms during the visit | 15 days of medication | 30 days of medication |
|---|---|---|---|
| 1 | Floaters: moderate vitreous opacity, 5-6 floating black dots in front of the eyes, floating with the rotation of the eyeball, and the observation of the white background such as ceilings and walls was affected. | The floating black dots were shallower than before the medication, the observation of the white background such as ceilings and walls was clearer than before the medication, and the contrast sensitivity was improved. | The black dots almost disappeared, and the visual quality such as contrast sensitivity was improved significantly. |
| 2 | Floaters: moderate vitreous opacity, 6-7 floating black dots in front of the eyes, dust-like floating objects in the anterior vitreous body can be seen under the slit lamp, and the observation of the white background such as ceilings and walls was affected. | The floating black dots were reduced to 2-3, the floating objects in the anterior vitreous body were reduced, the observation of the white background such as ceilings and walls was clearer than before the medication, and the contrast sensitivity was improved. | The black dots almost disappeared, the floating objects in the anterior vitreous body basically disappeared, and the visual quality such as contrast sensitivity was improved significantly. |
| 3 | Floaters: mild vitreous opacity, 3-4 floating black dots in front of the eyes, and the observation of the white background such as ceilings and walls was affected. | The floating black dots were shallower than before the medication, and the observation of the white background such as ceilings and walls was clearer than before the medication, and the contrast sensitivity was improved. | The black dots disappeared, and the visual quality such as contrast sensitivity was improved significantly. |
| 4 | Floaters: mild vitreous opacity, 2-3 floating black dots in front of the eyes, and the observation of the white background such as ceilings and walls was affected. | The floating black dots were significantly shallower than before the medication, the observation of the white background such as ceilings and walls was clearer than before the medication, and the contrast sensitivity was improved. | The black dots disappeared, the vision was clearer, and the visual quality such as contrast sensitivity was improved significantly. |
| 5 | Floaters: moderate vitreous opacity, 8-9 floating black dots in front of the eyes, floating with the rotation of the eyeball, dust-like floating objects in the anterior vitreous body can be seen under the slit lamp, and the observation of the white background such as ceilings and walls was blurred. | The floating black dots were shallower than before the medication, and the number was reduced to 3-4, the floating objects in the anterior vitreous body were reduced, the observation of the white background such as ceilings and walls was clearer than before the medication, and the contrast sensitivity was improved. | The black dots almost disappeared, the floating objects in the anterior vitreous body basically disappeared, and the visual quality such as contrast sensitivity was improved significantly. |
| 6 | Floaters: moderate vitreous opacity, 7-8 floating black dots in front of the eyes, 1 band of transparent opacity, the observation of the white background such as ceilings and walls was affected greatly, and there was visual disturbance. | The floating black dots and bands were shallower than before the medication, the observation of the white background such as ceilings and walls was clearer than before the medication, and the contrast sensitivity was improved. | The black dots and bands almost disappeared, the observation of the white background such as ceilings and walls was not affected, and the visual quality such as contrast sensitivity was improved significantly. |
| 7 | Floaters: mild vitreous opacity, 4-5 floating black dots in front of the eyes, floating with the rotation of the eyeballs, and the observation of the white background such as ceilings and walls was affected. | The floating black dots were shallower than before the medication, and the observation of the white background such as ceilings and walls was clearer than before the medication, and the contrast sensitivity was improved. | The black dots almost disappeared, the observation of the white background such as ceilings and walls was not affected, and the visual quality such as contrast sensitivity was improved significantly. |
| 8 | Floaters: moderate vitreous opacity, 4-5 floating black dots in front of the eyes, 1-2 bands of transparent opacity, and the observation of the white background such as ceilings and walls was affected greatly. | The floating black dots and bands were shallower than before the medication, the observation of the white background such as ceilings and walls was clearer than before the medication, and the contrast sensitivity was improved. | The black dots disappeared, the bands almost disappeared, and the visual quality such as contrast sensitivity was improved significantly. |
| 9 | Floaters: mild vitreous opacity, 3-4 floating black dots in front of the eyes, and the observation of the white background such as ceilings and walls was affected or interfered. | The floating black dots were shallower than before the medication, the observation of the white background such as ceilings and walls was clearer than before the medication, and the contrast sensitivity was improved. | The black dots almost disappeared, and the visual quality such as contrast sensitivity was improved significantly. |

It can be seen from the therapeutic effects shown in Table 2 that the pharmaceutical composition provided according to the present invention can make the black dots and bands in front of the eyes obviously shallow and/or less after about 15 days of medication, and improve the contrast sensitivity. About 30 days of medication, the pharmaceutical composition can make the black dots and bands in front of the eyes almost disappear, or even disappear completely, and the visual quality such as contrast sensitivity is significantly improved, and the floaters are basically cured, and there are no other side effects.

Although the present invention has been described in details with general description, specific embodiments and tests, some modifications or improvements which are obvious to those skilled in the art can be made on the basis of the present invention. Therefore, these modifications or improvements not deviating from the spirit of the present invention belong to the scope of protection claimed by the present invention.

What is claimed is:

1. A pharmaceutical composition, wherein the pharmaceutical composition comprises the following components:

a compound of formula I, hydroxypropyl methylcellulose, benzalkonium chloride, a pH regulator, and a solubilizer;

formula I

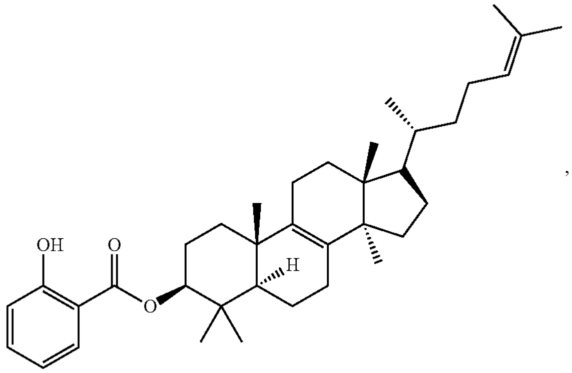

, wherein the pharmaceutical composition comprises the components with the following parts by weight:

0.01-4 parts of compound of formula I, 2-12 parts of hydroxypropyl methylcellulose, 0.05-0.06 parts of benzalkonium chloride, 1-20 parts of pH regulator, and 10-50 parts of solubilizer, and the pH of the pharmaceutical composition is 6 to 8; and wherein the pH regulator is selected from boric acid and borax, and the solubilizer is selected from the group consisting of polysorbate-80, glycerol, and hydrogenated castor oil-RH40.

2. The pharmaceutical composition according to claim 1, wherein a concentration of the compound of formula I in the pharmaceutical composition is 0.01~4 mg/mL.

3. The pharmaceutical composition according to claim 2, wherein the concentration of the compound of formula I in the pharmaceutical composition is 0.1 mg/mL, 0.2 mg/mL, 0.3 mg/mL, 0.4 mg/mL, 0.5 mg/mL, 1 mg/mL, 2 mg/mL, 3 mg/mL or 4 mg/mL.

4. The pharmaceutical composition according to claim 1, wherein the pharmaceutical composition comprises the components with the following parts by weight:

2 parts of compound of formula I, 6 parts of hydroxypropyl methylcellulose, 16.5 parts of boric acid, 2 parts of borax and 0.05 parts of benzalkonium chloride; or 2 parts of compound of formula I, 6 parts of hydroxypropyl methylcellulose, 40 parts of polysorbate-80, 16 parts of boric acid, 1.6 parts of borax and 0.05 parts of benzalkonium chloride; or 2 parts of compound of formula I, 6 parts of hydroxypropyl methylcellulose, 10 parts of hydrogenated castor oil-RH40, 17 parts of boric acid, 1.7 parts of borax and 0.05 parts of benzalkonium chloride.

5. The pharmaceutical composition according to claim 1, wherein a particle size of the compound of formula I is <90 μm, and/or the particle size distribution of the compound of formula I is $D_{90} \leq 7$ μm and/or $D_{50} \leq 4$ μm.

6. The pharmaceutical composition according to claim 1, wherein a dosage form of the pharmaceutical composition is a suspension, an emulsion or a gel.

7. A preparation method for the pharmaceutical composition according to claim 1, wherein the preparation method comprises: mixing evenly the compound of formula I, hydroxypropyl methylcellulose, benzalkonium chloride, the pH regulator and the solubilizer according to a prescription amount to obtain the pharmaceutical composition.

8. The preparation method according to claim 7, wherein the preparation method comprises the following steps:

(1) dissolving hydroxypropyl methylcellulose with water for injection to obtain solution I;

(2) dissolving the components other than hydroxypropyl methylcellulose and the compound of formula I in prescription amount with water for injection, then adding to the solution I, and mixing evenly to obtain solution II;

(3) taking a prescription amount of the compound of formula I, adding to the solution II, and mixing evenly to obtain solution III; and (4) filling the solution III to full volume with water for injection to obtain the pharmaceutical composition.

9. A method for the prevention or treatment of cataracts or floaters, comprising administering the pharmaceutical composition according to claim 1 to a subject in need thereof.

10. The pharmaceutical composition according to claim 1, wherein a particle size of the compound of formula I is <50 μm.

11. The pharmaceutical composition according to claim 1, wherein the dosage form of the pharmaceutical composition is an emulsion.

12. A pharmaceutical composition, wherein the pharmaceutical composition comprises the components with the following parts by weight:

2 parts of compound of formula I, 6 parts of hydroxypropyl methylcellulose, 25 parts of glycerol and 0.05 parts of benzalkonium chloride; or 2 parts of compound of formula I, 6 parts of hydroxypropyl methylcellulose, 10 parts of hydrogenated castor oil-RH40, 40 parts of polysorbate-80, 25 parts of glycerol, and 0.05 parts of benzalkonium chloride, formula I

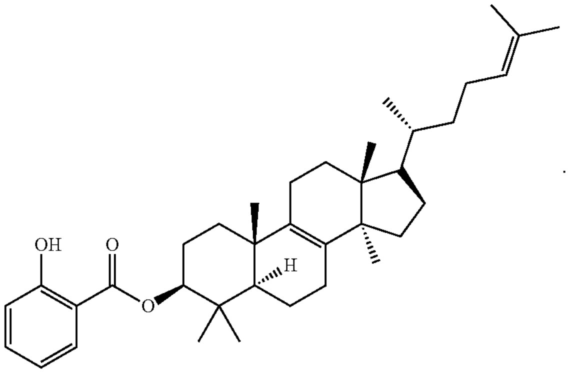

13. The pharmaceutical composition according to claim 12, wherein a particle size of the compound of formula I is <90 μm, and/or the particle size distribution of the compound of formula I is $D_{90}\leq 7$ μm and/or $D_{50}\leq 4$ μm.

14. The pharmaceutical composition according to claim 13, wherein the particle size of the compound of formula I is ≤50 μm.

15. The pharmaceutical composition according to claim 12, wherein a dosage form of the pharmaceutical composition is a suspension, an emulsion or a gel.

16. The pharmaceutical composition according to claim 15, wherein the dosage form of the pharmaceutical composition is an emulsion.

17. A method for the prevention or treatment of cataracts or floaters, comprising administering the pharmaceutical composition according to claim 12 to a subject in need thereof.

* * * * *